United States Patent [19]
Munro et al.

[11] Patent Number: 5,831,101
[45] Date of Patent: Nov. 3, 1998

[54] 14-METHYL-HEXADECENOLIDE AND 14-METHYL-HEXADECANOLIDE

[75] Inventors: David Munro, Maidstone; Charles Stanley Sell, Aldington, both of United Kingdom

[73] Assignee: Quest International B.V., Naarden, Netherlands

[21] Appl. No.: 967,166

[22] Filed: Nov. 10, 1997

[30] Foreign Application Priority Data

Nov. 8, 1996 [EP] European Pat. Off. .............. 96308107

[51] Int. Cl.$^6$ ............................. C07D 313/00; A61K 7/46
[52] U.S. Cl. ............................. 549/266; 549/271; 512/11
[58] Field of Search ................................... 549/266, 271; 512/11

[56] References Cited

U.S. PATENT DOCUMENTS 3,907,831  9/1975  Becker .
5,726,328  3/1998  Mane et al. ............................. 549/266

FOREIGN PATENT DOCUMENTS 1221105  4/1987  Canada .
2410859  9/1975  Germany .

*Primary Examiner*—Bernard Dentz
*Attorney, Agent, or Firm*—Pillsbury Madison & Sutro LLP

[57] ABSTRACT

The invention concerns 14-methyl-hexadecen-11-olide, 14-methyl-hexadecen-12-olide and 14-methyl-hexadecanolide and the use of these compounds as fragrance materials with musk odour. The invention also concerns 14-methyl-12-hydroxy-hexasecanolide, which is an intermediate in a novel process to prepare these compounds.

9 Claims, No Drawings

14-METHYL-HEXADECENOLIDE AND 14-METHYL-HEXADECANOLIDE

The invention concerns 14-methyl-hexadecen-11-olide, 14-methyl-hexadecen-12-olide and 14-methyl-hexadecanolide and the use of these compounds in perfumery. The invention also concerns a process for the preparation of these compounds as well as the compound 12-hydroxy-14-methyl-hexadecanolide and its use as an intermediate in the process.

Many macrolactones, particularly C14–C16 lactones are known in the art and many have been described as having to a greater or lesser extent a musk-like odour. However, these odours differ considerably in quality as well as musk intensity and only a few have so far found practical use in perfumery. Thus, Hexadecen-7-olide, also known as Ambrettolide, is a well known fragrance material with a musky-floral odour (S. Arctander Perfume and Flavour Chemicals, monograph 105), while its isomers with the double bond in the 5 or 6 position only have a faint musky odour and are of no more than academic interest (S. Arctander, monographs 106 and 107). Pentadecanolide (S. Arctander, monograph 811) is probably one of the most extentively used macrocyclic musk materials and is marked under many tradenames. Hexadecanolide (S. Arctander, monograph 923) is again a well known musk fragrance material.

In DE-A-2026056 a process for the preparation of various C14–C17 lactones is described. The lactones may be substituted by a methyl group in the 1 or 2 position counted from the ring oxygen atom and may have a double bond in various positions in the ring. The compounds are said to develop (quote) "a more or lesser characteristic musk-like odour". From the Examples it is clear that the process is primarily intended to provide an new route to the well known pentadecanolide. 14-Methyl-tetradecanolide and 14-methyl-tetradecen-(11 and 12)-olide are also described therein as having interesting odour properties without further indicating the nature of these properties. Furthermore 15-methyl- and 14-methyl-pentadecanolides as well as pentadecen-(11 and 12)-olides were prepared without any indication of possible use in perfumery.

In DE-A-2410859 a process is described for preparing macrocyclic ketolactones, which may be substituted by methyl or ethyl groups. Whereas various macrocyclic ketolactones have been described as strong and agreeable musk odorants (Ohloff, Fortschritte der chem Forschung 12, (1969) 203) it can be seen from the table 1 in DE-A-2410859 that the odour properties vary considerably and unpredictably with the actual structure.

In CA 1 221 105 a number large number of saturated and unsaturated, unsubstituted and methyl-substituted lactones of 14–17 ring carbon atoms are mentioned. It is said that such compounds generally are musk odorants without specifying their odour properties or quality, since the inventors were only interested in the use of these compounds as starting materials for ω-halogenated fatty acids.

In spite of extensive efforts to find alternative and easily available macrolactone musk fragrance materials, only the few ones mentioned above by Arctander (monographs 105, 811 and 923) as well as 11- and 12-oxahexadecanolide have so far found any practical use in perfumery.

However, there is a need in perfumery for novel musk fragrance materials with comparable or better odour properties than the ones which are presently used. Also, they should preferably be easy to prepare.

It has now been found that 14-methyl-hexadecen-11-olide and 14-methyl-hexadecen-12-olide of formulae 1a and b (in which the wavy lines indicate cis and trans isomers) and 14-methyl-hexadecanolide of formula 2 below are valuable fragrance materials with a strong and agreeable musk odour.

The compounds furthermore are characterized by fiber substantivity properties which are exceptional for macrocyclic musk fragrance materials and in this respect they equal or even surpass the polyclic musks.

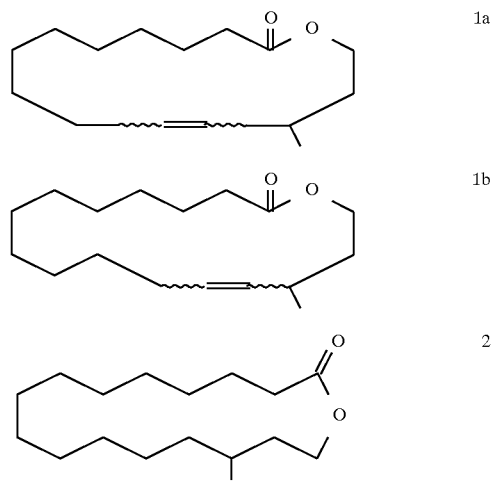

The compounds have not previously been described in the prior art. Accordingly, the invention provides the novel compounds 14-methyl-hexadecen-11-olide and 14-methyl-hexadecen-12-olide of formula 1a,b and 14-methyl-hexadecanolide of formula 2 as well as perfumes and perfumed products containing one or more of these compounds. From a perfumery point of view 14-methyl-hexadecen-11-olide, 14-methyl-hexadecen-12-olide are preferred.

The musk lactones of the present invention can be made via route analogous to those described in the art. Thus, they may be prepared using the bicyclic enol ether of formula 3 below as the starting material. This compound may be transferred into a an oxabicyclic hydroperoxide or a symmetric oxabicyclic peroxide and subsequently thermally or photochemically decomposed, analogous to the procedure described in DE-A-2026056. Alternatively, the bicyclic enol ether may be oxidized to obtain 14-methyl-12-oxo-hexadecanolide of formula 4 below. This may be done by ozonolysis as described in DE-A-2410859, or alternatively using sodium periodate/ruthenium chloride. 14-Methyl-12-oxo-hexadecanolide can be converted into a mixture of 14-methyl-hexadecen-11-olide and 14-methyl-hexadecen-12-olide according to a novel process involving reduction to 14-methyl-12-hydroxy-hexadecanolide of formula 5 below, followed by dehydration. The mixture of both unsaturated musk lactones according to the invention (both in cis and trans form) which is thus obtained may be separated into its components according to standard separation procedures such as glc or hplc. From a perfumery point of view such separation is unnecessary and the mixture can be used as such. Catalytic hydrogenation of the mixture yields 14-methyl-hexadecanolide.

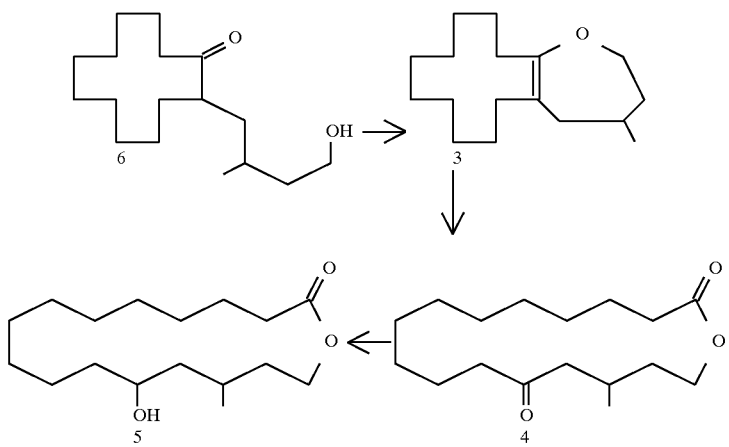

The bicyclic enol ether (3) may be prepared through reaction of a mixture of cyclododecanone and isoprenol with di-tert.butylperoxide followed by ring closure of the keto-alcohol with formula 6 with phosphoric acid.

14-Methyl-12-hydroxy-hexadecanolide is a novel compound and an important intermediate in the novel process to obtain the musk lactones of the present invention. The invention therefore also comprises this compound and its use as an intermediate in the synthesis.

The musk lactones according to the invention may be used as such to impart, strengthen or improve the odour of a wide variety of products, or they may be used separately or in combinations of two or three of them as a component of a perfume to contribute its odour character to the overall odour of such perfume. For the purposes of this invention a perfume is intended to mean a mixture of fragrance materials, if desired mixed with or dissolved in a suitable solvent or mixed with a solid substrate, which is used to impart a desired odour to the skin and/or any product for which an agreeable odour is indispensible or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders, body deodorants and antiperspirants, etc.

Other fragrance materials which can be advantageously combined with the musk lactones according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitrites, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with the musk lactones according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl) propanal, 3-(p-tert-butylphenyl)-propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pentenyl)-3-cyclohexenecarboxaldehyde, 4-acetoxy-3-pentyltetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphyl-cyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, other macrolactone musks, ethylene brassylate.

Solvents which can be used for perfumes which contain the alcohol according to the invention are, for example: ethanol, isopropanol, diethyleneglycol monoethyl ether, dipropylene glycol, diethyl phthalate, triethyl citrate, isopropyl myristate, etc.

The quantities in which the musk lactones according to the invention can be used in perfumes or in products to be perfumed may vary within wide limits and depend, inter alia, on the nature of the product, on the nature and the quantity of the other components of the perfume in which the compound is used and on the olfactive effect desired. It is therefore only possible to specify wide limits, which, however, provide sufficient information for the specialist in the art to be able to use the musk lactones according to the invention for his specific purpose. In perfumes an amount of 0.01% by weight or more of the musk lactones according to the invention will generally have a clearly perceptible olfactive effect. Preferably the amount is 0.1% or more, but generally not more than 40% by weight, more preferably at least 1%. The amount of the musk lactones according to the invention present in products will generally be at least 0.1 ppm by weight, preferably at least 1 ppm, more preferably at least 10 ppm.

However, levels of up to about 10% by weight may be used in particular cases, depending on the product to be perfumed.

EXAMPLE 1

Preparation of 2-(4-hydroxy-2-methybutyl)-1-cyclododecanone form cyclododecanone and isoprenol Cyclododecanone (218 g, 1.2 mol) and isoprenol (34.4 g, 0.4 mol) were mixed with tert-butylperoxide (10 g) and the mixture was heated at 180° C. for 6 hrs. The product was purified by column chromatography to yield recovered cyclododecanone (176 g) and a colourless oil (20.9 g). Yield of the hydroxyketone is 34% based on recovered cyclododecanone.

Preparation of 4-methyl-2,3,4,5,6,7,8,9,10,11,12,13,14,15-tetradecahydrocyclododeca[b]oxepine The hydroxyketone (41.3 g) was added to a 100 m flask equiped with a vigreux, and 5 drops of orthophosphoric acid were added. The reaction mixture was subjected to vacuum distillation at 130° C. at 20 mbar for 1 hour, removing the water formed. The vacuum was increased to 3 mbar and the internal temperature raised until a product distilled over.

Bp=145° C. at 3 mbar. Yield of bicyclic enol ether is 28.1 g (71%)

Preparation of 14-methyl-12-oxohexadecanolide

To the enol ether (2.10 g, 8.4 mmol) in $CCl_4$ (20 ml), acetonitrile (20 ml), and water (30 ml) at room temperature was added sodium metaperiodate (6.75 g, 35.3 mmol) followed by ruthenium chloride hydrate (50 mg). The mixture was stirred vigourously and an exotherm was noted (approx 5° C.). Once the exotherm had subsided the dark/opaque solution was checked with TLC (9:1, hexane/ethylacetate) which showed the reaction to be complete after 15 minutes. To the reaction mixture was added a 1:1 mixture of dichloromethane and water (60 ml). The organic fractions were separated and dried and the solvent evaporated under reduced pressure to yield a dark oil. The oil was purified by column chromatography, eluting the product with 10% diethyl ether in pentane. The product is a colourless to pale yellow oil. Yield is 1.64 g (69%).

Preparation of 12-hydroxy-14-methylhexadecanolide

To a solution of 1,34 g of the ketolactone (4.7 mmol) in 12 ml of a mixture of THF (5 parts), acetic acid (glacial, 1 part) was added 0.33 g of sodium cyanoborohydride (5.2 mmol). The resulting clear and colourless solution was left to stir whilst being followed by TLC (9:1, hexane/ethylacetate). The reaction was complete after 2 hours, and the reaction mixture was poured into diethylether and washed with saturated sodium bicarbonate, followed by water. The organic fraction was dried and the solvent evaporated under reduced pressure to yield a colourless oil which was 95.26% pure hydroxylactone by GC. Yield was 1.32 g (98%).

Preparation of 14-methylhexadecen-11/12-olide

The hydroxylactone (0.97 g) was heated at reflux in hexamethylphosphorus triamide (10 ml) for 1.5 hrs. The cooled solution was dissolved in hexane containing 5% diethylether and washed with brine (three times), dried and concentrated under reduced pressure. The crude product was purified by column chromatography to yield a colourless oil. Yield was 0.67 g (74%).

We claim:
1. 14-methyl-hexadecen-11-olide.
2. 14-methyl-hexadecen-12-olide.
3. 14-methyl-hexadecanolide.
4. A mixture of 14-methyl-hexadecen-11-olide and 14-methyl-hexadecen-12-olide.
5. 14-methyl-12-hydroxy-hexadecanolide.
6. Perfume compositions comprising a musk lactone characterized in that it comprises at least one musk lactone according to claims 1–3.
7. Perfume compositions according to claim 6 characterized in that contains between 0.01 and 40% by weight of the musk lactone according to claims 1–3.
8. Perfumed products containing a musk lactone characterized in that it contains at least one musk lactone according to claims 1–3.
9. Perfumed product according to claim 8 characterized in that it contains at least 0.1 by weight of the musk lactone according to claims 1–3.

\* \* \* \* \*